United States Patent
Andrus

(10) Patent No.: US 10,279,092 B2
(45) Date of Patent: May 7, 2019

(54) ANCHORED MOUNTING RING

(71) Applicant: HeartWare, Inc., Miami Lakes, FL (US)

(72) Inventor: Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 12 days.

(21) Appl. No.: 14/519,850

(22) Filed: Oct. 21, 2014

(65) Prior Publication Data

US 2015/0112120 A1 Apr. 23, 2015

Related U.S. Application Data

(60) Provisional application No. 61/894,117, filed on Oct. 22, 2013.

(51) Int. Cl.
| | |
|---|---|
| *A61M 1/10* | (2006.01) |
| *A61M 1/12* | (2006.01) |
| *A61B 17/34* | (2006.01) |

(52) U.S. Cl.
CPC ... *A61M 1/1008* (2014.02); *A61B 2017/3425* (2013.01); *A61B 2017/3488* (2013.01); *A61M 1/12* (2013.01); *A61M 1/122* (2014.02); *A61M 2205/04* (2013.01); *A61M 2210/125* (2013.01)

(58) Field of Classification Search
CPC ....... A61M 1/10; A61M 1/1008; A61M 1/122
See application file for complete search history.

(56) References Cited

U.S. PATENT DOCUMENTS

| | | | |
|---|---|---|---|
| 2,168,988 A * | 8/1939 | Hultquist | F16M 11/14 248/181.1 |
| 3,371,352 A | 3/1968 | Sippos et al. | |
| 5,540,648 A * | 7/1996 | Yoon | A61B 17/3403 600/102 |
| 5,695,504 A | 12/1997 | Gifford, III et al. | |

(Continued)

FOREIGN PATENT DOCUMENTS

| | | |
|---|---|---|
| WO | 02054958 A1 | 7/2002 |
| WO | 2014117087 A1 | 7/2014 |

OTHER PUBLICATIONS

International Search Report and Written Opinion for Application No. PCT/US2014/061575 dated Feb. 20, 2015.

(Continued)

*Primary Examiner* — Eugene T Wu
(74) *Attorney, Agent, or Firm* — Christopher & Weisberg, P.A.

(57) ABSTRACT

A mounting ring for a ventricular assist device or other device used in the heart includes a plate adapted to be secured to the exterior of the heart by rigid anchors such as hook, pin, or screw. When hooks are used, they can be pivotally mounted to the plate so that the hooks can rotate from retracted positions to advanced positions. A tool can be included in a mounting ring kit to move the hooks from their retracted positions to their advanced positions so that the hooks secure the plate to the heart. Preferably, all of the hooks are advanced simultaneously. The VAD or other device is then secured to the plate. The plate can be mounted to the heart in less time than required to install a traditional mounting ring by suturing to the heart.

13 Claims, 21 Drawing Sheets

(56) References Cited

U.S. PATENT DOCUMENTS

| | | | |
|---|---|---|---|
| 5,728,116 A * | 3/1998 | Rosenman | A61B 17/0401 606/151 |
| 6,074,418 A | 6/2000 | Buchanan et al. | |
| 6,106,550 A | 8/2000 | Magovern et al. | |
| 6,332,893 B1 | 12/2001 | Mortier et al. | |
| 6,402,780 B2 | 6/2002 | Williamson, IV et al. | |
| 6,797,002 B2 | 9/2004 | Spence et al. | |
| 7,097,659 B2 | 8/2006 | Woolfson et al. | |
| 7,172,625 B2 | 2/2007 | Shu et al. | |
| 7,226,477 B2 | 6/2007 | Cox | |
| 7,311,730 B2 | 12/2007 | Gabbay | |
| RE40,377 E | 6/2008 | Williamson, IV et al. | |
| 7,404,824 B1 | 7/2008 | Webler et al. | |
| 7,722,667 B1 | 5/2010 | Buchanan | |
| 7,896,913 B2 | 3/2011 | Damm et al. | |
| 7,922,762 B2 | 4/2011 | Starksen | |
| 7,959,674 B2 | 6/2011 | Shu et al. | |
| 8,021,421 B2 | 9/2011 | Fogarty et al. | |
| 8,070,804 B2 | 12/2011 | Hyde et al. | |
| 8,092,525 B2 | 1/2012 | Eliasen et al. | |
| 8,167,936 B2 | 5/2012 | Kurian | |
| 8,241,351 B2 | 8/2012 | Cabiri | |
| 8,366,769 B2 | 2/2013 | Huynh et al. | |
| 8,470,028 B2 | 6/2013 | Thornton et al. | |
| 8,506,532 B2 | 8/2013 | Olroyd et al. | |
| 8,518,107 B2 | 8/2013 | Tsukashima et al. | |
| 8,545,553 B2 | 10/2013 | Zipory et al. | |
| 8,579,790 B2 * | 11/2013 | Jeffery | A61M 1/12 600/16 |
| 8,663,249 B2 | 3/2014 | Badhwar | |
| 8,827,887 B2 | 9/2014 | Curtis et al. | |
| 2004/0245416 A1 * | 12/2004 | Attee | B25B 5/147 248/214 |
| 2007/0179558 A1 * | 8/2007 | Gliner | A61N 1/36082 607/45 |
| 2009/0171136 A1 | 7/2009 | Shambaugh, Jr. | |
| 2009/0319038 A1 | 12/2009 | Gurskis et al. | |
| 2010/0312335 A1 | 12/2010 | Kurian | |
| 2011/0224785 A1 * | 9/2011 | Hacohen | A61B 17/0401 623/2.18 |
| 2011/0230962 A1 | 9/2011 | Moaddeb et al. | |
| 2012/0221021 A1 | 8/2012 | Hoarau et al. | |
| 2012/0245604 A1 | 9/2012 | Tegzes | |
| 2013/0047790 A1 * | 2/2013 | Shah | B23P 19/069 81/57.22 |
| 2013/0060267 A1 | 3/2013 | Farnan et al. | |
| 2016/0121033 A1 * | 5/2016 | Cotter | A61M 1/1008 623/3.26 |

OTHER PUBLICATIONS

Partial International Search Report for Application No. PCT/US2014/061575 dated Dec. 23, 2014.
Apica Technology, "The Apica ASC system", <http://www.apica.ie/apica-technology.html>, Copyright 2013.

* cited by examiner

ANCHORED MOUNTING RING

CROSS-REFERENCE TO RELATED APPLICATIONS

This application claims the benefit of the filing date of U.S. Provisional Patent Application No. 61/894,117, filed Oct. 22, 2013, the disclosure of which is hereby incorporated by reference herein.

BACKGROUND OF THE INVENTION

The present invention relates to components and methods used for mounting devices such as ventricular assist devices and associated elements to the heart of a living subject.

The heart is sometimes incapable of providing sufficient pumping capacity to meet the needs of the body. The effects of this inadequacy can be alleviated by providing a mechanical pump referred to as a ventricular assist device ("VAD") to supplement the pumping action of the heart. It is preferable for a VAD to have the ability to be implanted in a patient to supplement or replace the pumping action of the heart for an extended period of time. A patient may have a VAD for years while awaiting a suitable donor for a heart transplant.

A VAD is most commonly connected to the left ventricle. Most VADs have an outlet tube which is connected to the aorta. During operation, the VAD assists the heart to pump blood from the left ventricle to the ascending or descending aorta.

The VAD is typically connected to the heart through the use of a mounting ring, as disclosed in U.S. Published Patent Application Nos. 2004/0171905 and 2007/0134993, the disclosures of which are hereby incorporated by reference herein. Sutures are commonly used to secure the mounting ring to the exterior of the heart.

A separate surgical tool is then used to cut a hole in the heart within the mounting ring opening. The VAD, or an inlet tube connected to the VAD, is then connected to the left ventricle and secured to the mounting ring by a VAD connector. The seal between the heart and mounting ring must be sufficiently tight to prevent blood loss from the heart. Also, the attachment between the heart and the ring must remain secure despite mechanical stresses. The attachment procedure should not cause unacceptable damage to the wall of the heart. Suturing the mounting ring to the heart takes considerable time during the installation procedure. It would also be desirable to reduce the time taken to secure the ring to the heart.

Therefore, a need exists for an improved apparatus and method for mounting a VAD or other device to the heart.

BRIEF SUMMARY OF THE INVENTION

A mounting ring kit according to one aspect of the disclosure may include a plate having a proximal side, a distal side adapted to be placed against an exterior surface of a heart, and an opening extending through the plate from the proximal side to the distal side. Passageways can extend through the plate from the proximal side to the distal side and rigid anchors may be at least partially disposed within the passageways. The rigid anchors can be movable from a first retracted position towards an advanced position in which the anchors project from the distal side of the plate.

A mounting ring kit may further include a sealing ring on the distal side of the plate extending around the opening. In some embodiments, the anchors may be a screw, hook, or pin and can be configured to pull tissue of the heart to the distal side of the plate. A mounting ring kit can have anchors projecting from the proximal side of the plate when the anchors are in the retracted position. A mounting ring kit may also include an adaptor configured to be attached to the plate and positioned adjacent the proximal side of the plate and overlie the anchors in the second position to lock the anchors in the second position. In at least one embodiment, a mounting ring kit includes a locking element to lock the anchors in the second position, wherein the locking element includes a barb, arm bar lock, or a spring lock. Housings may be coupled to the distal side of the plate and aligned with each of the passageways. The passageways may extend at least partially through the housing and be disposed at an angle oblique to the proximal-to-distal axis formed by the opening. In some embodiments, the plurality of anchors are mounted to the plate for pivoting motion about rotational axes transverse to the proximal-to-distal axis and the rotational axes may be tangent to a circle encircling the axis. An adaptor may further comprise an annular wall which can be detachable from the plate. A clamp may also be coupled to the annular wall.

In some embodiments, a mounting ring kit may include a tool for moving the anchors from the first position to the second position and may be adapted to simultaneously move more than one of the anchors. The plate may provide a mount for securing a device penetrating a wall of the heart.

A mounting ring according to one aspect of the disclosure may include a plate having an opening and a plurality of passageways; a plurality of anchors, each of which are pivotably connected to the plate to rotate about an axis tangent to a circle encircling the opening; and an annular wall adapted to be attached to the plate. The annular wall may be shaped to be positioned within the opening, attached to the plate, and locked to the plate by a bayonet lock. The anchors may include a hook, pin, screw, or any combination thereof. The anchors may extend away from the proximal side of the plate in a first position and extend from the distal side of the passageways in a second position to secure the distal side of the plate to the heart. The anchors may include a tip which is located at a first distance from the opening in the first position and a second distance from the opening in the second position. The first distance can be greater than or less than the second distance.

A method of installing a mounting ring according to one aspect of the disclosure includes obtaining a mounting ring having a proximal side, a distal side, an opening, a plurality of passageways extending through the mounting ring parallel to the opening, and anchors at least partially within the passageways. The method may also include obtaining a tool for inserting the anchors into a heart, accessing the heart, placing the distal side of the mounting ring adjacent to an external surface of the heart, inserting the anchors from a retracted position and into the heart. The anchors may be rigid anchors selected from at least one of a hook, pin, or screw. The method may further comprise rotating a hook about an axis and into the heart and may include inserting more than one anchor simultaneously.

BRIEF DESCRIPTION OF THE DRAWINGS

A more complete appreciation of the subject matter of the present invention and the various advantages thereof can be realized by reference to the following detailed description, in which reference is made to the accompanying drawings:

FIG. 21b illustrates a bottom perspective view of the plate of FIG. 21a.

DETAILED DESCRIPTION

Figure 2:
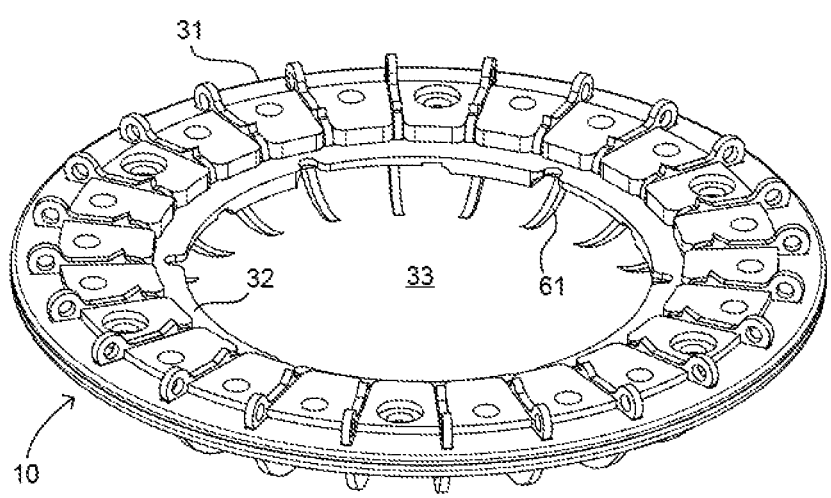
FIG. 2 is a perspective view of the plate of FIG. 1 with the hooks in a second position.
Figure 3:
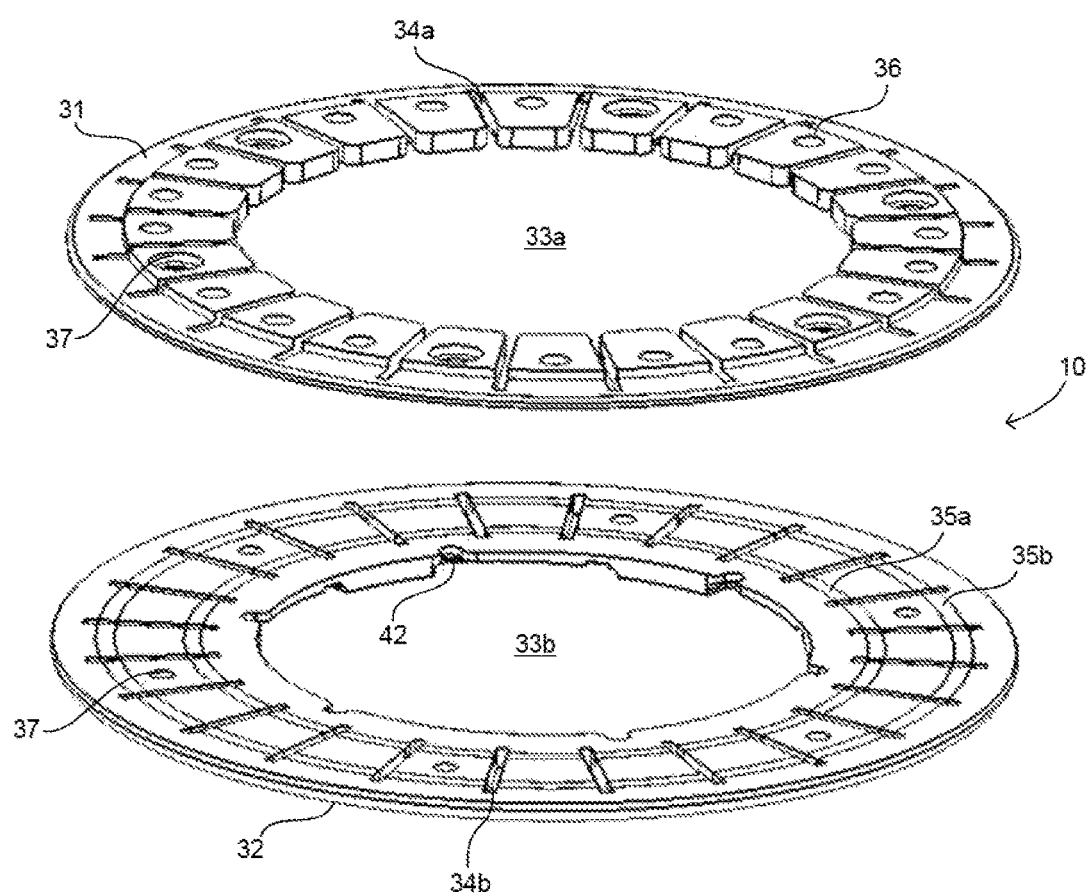
FIG. 3 illustrates an exploded view of the plate of FIG. 1.

A mounting ring according to one embodiment of the invention includes a plate 10 (FIG. 1) having a proximal surface 38 and a distal surface 39. Plate 10 is generally in the form of a disc having a central 192 axis extending in the proximal to distal direction. As best seen in FIG. 3, the plate 10 includes a first piece 31 defining the proximal surface and a second piece 32 defining the distal surface. The first piece 31 has passageways 34a and second piece 32 has corresponding passageways 34b. The passageways 34a and 34b of the first piece 31 and second piece 32 are generally aligned with one another to provide a plurality of passageways 34 (FIGS. 1 and 2) extending completely through the plate 10 when the first piece 31 and second piece 32 are joined together. Passageways 34a and 34b are narrow, elongated slots extending radially with respect to the central axis 192. Merely by way of example, the width $W_p$ of each passageway may be about 0.024 inches. The plate is preferably made of a biocompatible material such as a titanium alloy sold under the designation Ti-64, although other materials are also contemplated.

An opening 33a extends through the first piece 31, and a corresponding opening 33b extends through the second piece 32. When the pieces are assembled, openings 33a and 33b cooperatively form a central opening 33 extending through the plate 10 and concentric with axis 13. The opening 33b in the second piece 32 has a smaller diameter than the opening 33a in the first piece 31 as best seen in FIG. 2. The opening 33 is configured to receive an adaptor as explained below. Therefore, the size and shape of the opening 33 can be adjusted to accommodate any adaptor selected for use with the plate 10.

An inner channel 35a and outer channel 35b are formed on the proximal-facing side of second piece 32 as best seen in FIG. 3. Corresponding channels 35c and 35d (FIG. 13a) are formed on the distal-facing side of first piece 31.

Figure 1:
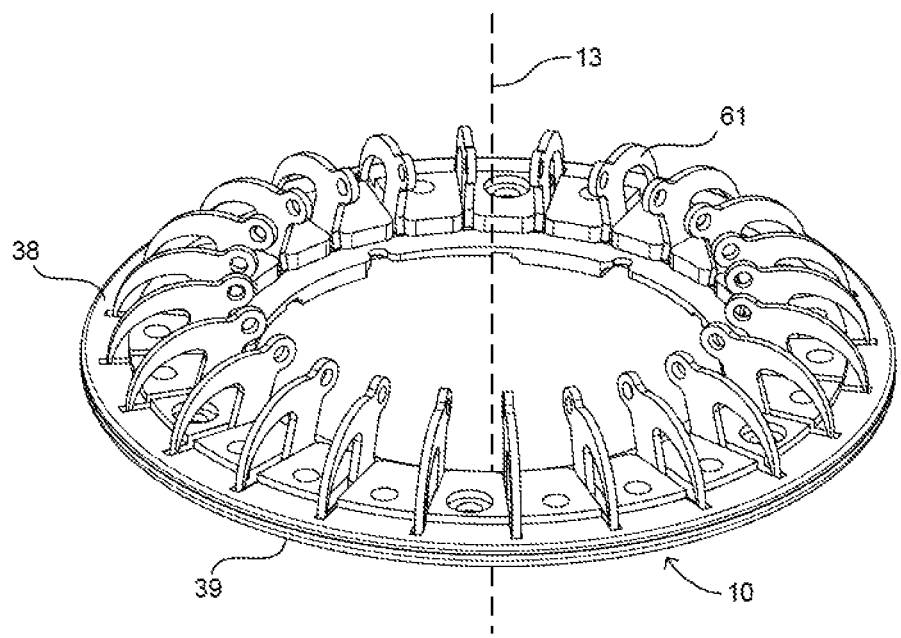
FIG. 1 is a perspective view of a plate with hooks in a first position in accordance with one embodiment of the current invention.
Figure 4:
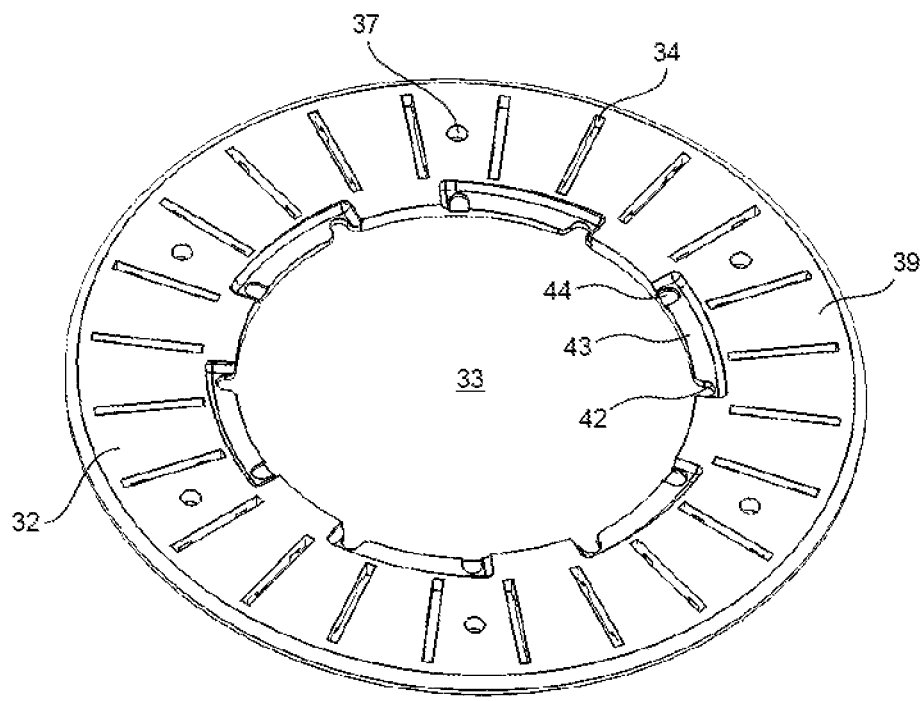
FIG. 4 illustrates a bottom view of the plate of FIG. 1.

Screw holes 37 are formed in the first and second pieces 31, 32 to accept screws to connect the pieces together. Additional holes 36 are also formed in the first piece 31 as a weight reducing feature. When the two pieces 31, 32 are joined together they form the plate 10 with the proximal side 38 adjacent the exterior of the first piece 31 and a distal side 39 adjacent the exterior of the second piece 32 (FIG. 1 and FIG. 4). Merely by way of example, the outer diameter of the first and second pieces may be about 1.84 inches.

As best shown in FIG. 4, a bayonet locking feature is formed on the distal side 39 of the second piece 32. The bayonet lock is formed by a notch 42 extending through the second piece 32, a ramp 43, and a pit 44. The ramp 43 extends between the notch 42 and pit 44 and increases from a first thickness adjacent the notch 42 to a second increased thickness adjacent the pit 44. The pit 44 has a depth less than that of the adjacent ramp portion. As explained in more detail below, the bayonet lock can be used to secure the plate to a tool or VAD connector.

Figure 5:
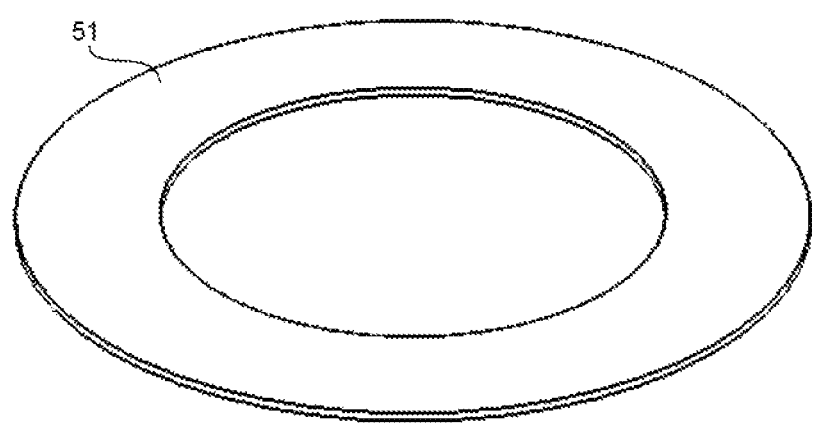
FIG. 5 illustrates a perspective view of a gasket used with the plate of FIGS. 1-4.

A gasket 51, best seen in FIG. 5, is adapted to be positioned between the distal side of the plate 10 and the heart. The gasket has a shape generally conforming to the shape of the plate 10 and is preferably made of a compressible material that provides a seal between the heart and the plate (e.g. silicone). In addition, the gasket may provide a spring locking feature to secure an adaptor to the plate.

Figure 6:
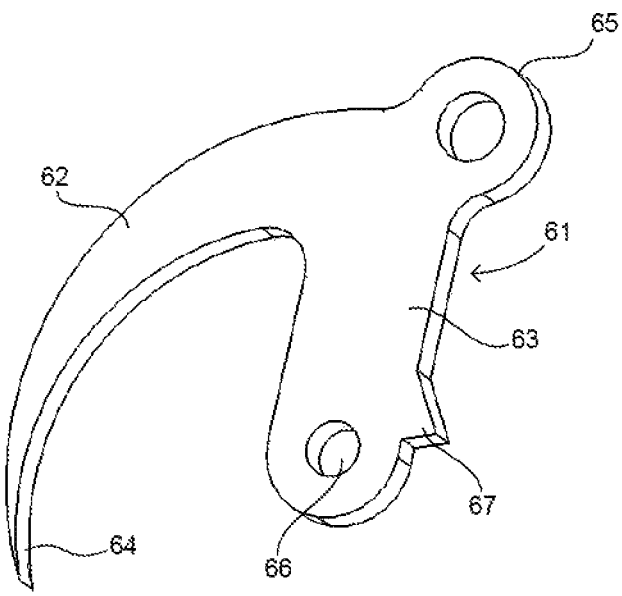
FIG. 6 illustrates a perspective view of a hook used with the plate of FIG. 1.
Figure 6A:
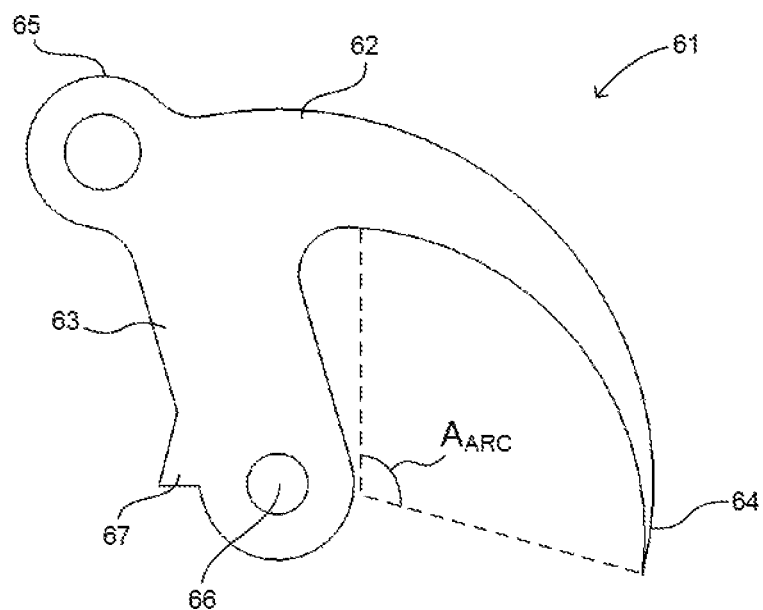
FIG. 6a illustrates a profile view of the hook of FIG. 1.

A plurality of anchors in the form of hooks 61 (FIGS. 1, 2 and 6) are movably mounted to plate 10. As best seen in FIG. 6, each hook 61 is a generally planar structure. Merely by way of example, the hook may be about 0.02 inches thick. Each hook has an elongated body 63 with an axle opening 66 adjacent one end of the body. An arm 62 projects from the body remote from axle opening 66. The arm 62 is generally in the form of an arc about an axis of curvature extending within or near axle opening 66, so that the hook 61 has a shape like a sickle. The angular extent $A_{ARC}$ of the arm about the axis of curvature is slightly more than 90°, desirably about 90-120°, as best seen in FIG. 6a. The arm 62 tapers into a sharp tip 64 as it extends away from the body 63. It is believed that the shape of the arm 62 enables the hook to pull tissue toward the body 63 as the hook is rotated as discussed below. A protuberance 65 extends from body 62 adjacent the intersection of the arm 62 and body 63. The protuberance 65 is adapted to be engaged by a tool to rotate the hook 61. A bump 67 juts out from the body 63. The bump 67 can help maintain the position of the hook 61 prior to deployment.

Figure 13:
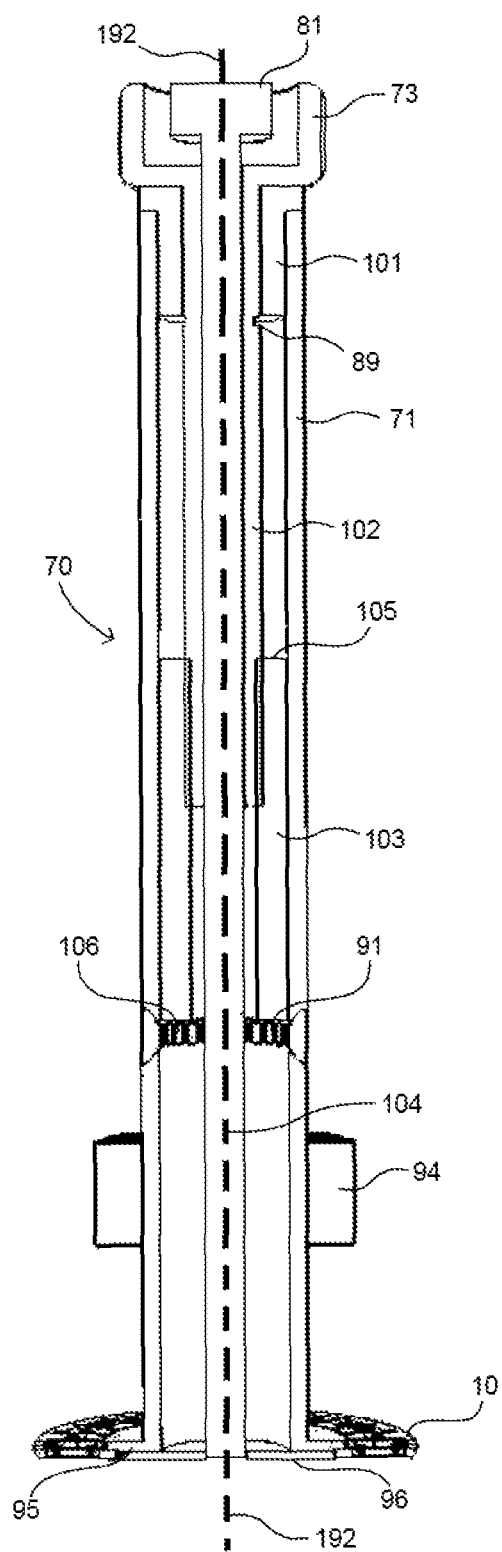
FIG. 13 illustrates a sectional view of the tool of FIG. 8.
Figure 13A:
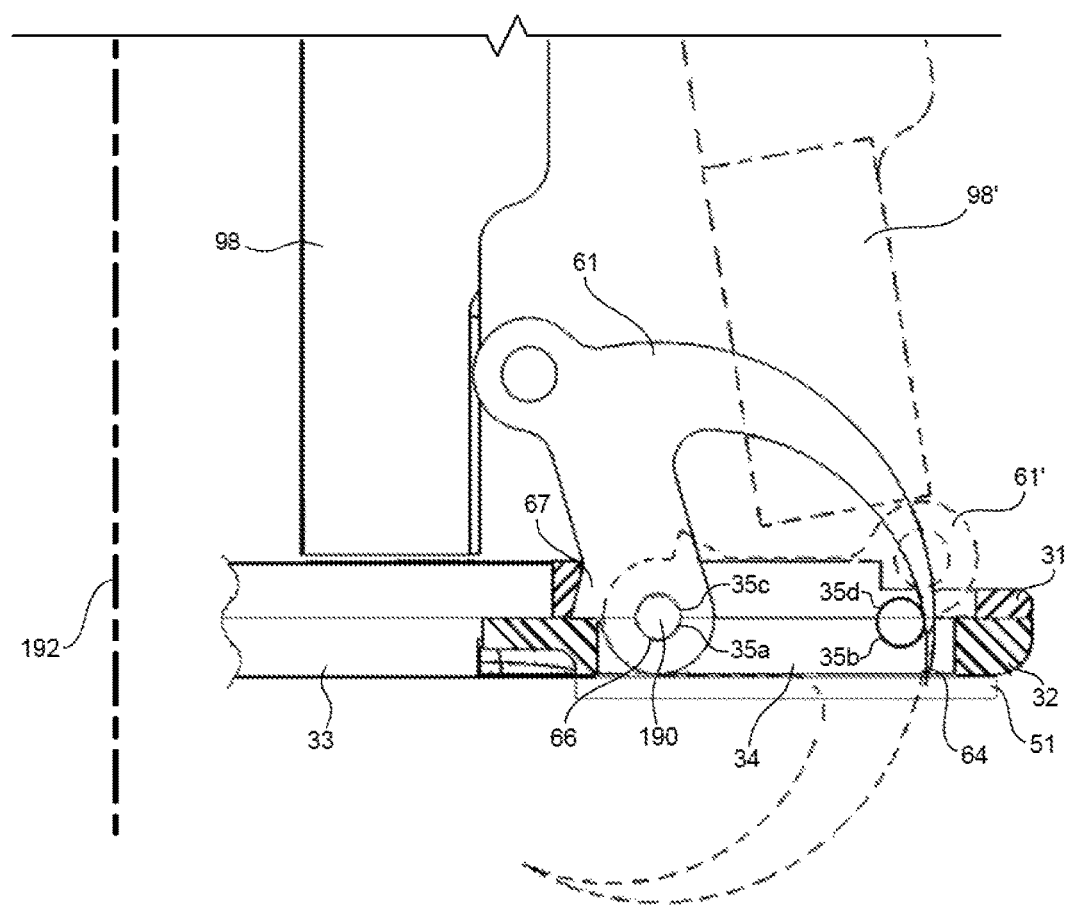
FIG. 13a is an enlarged sectional view of the hook, plate, and finger of FIG. 8.
Figure 14:
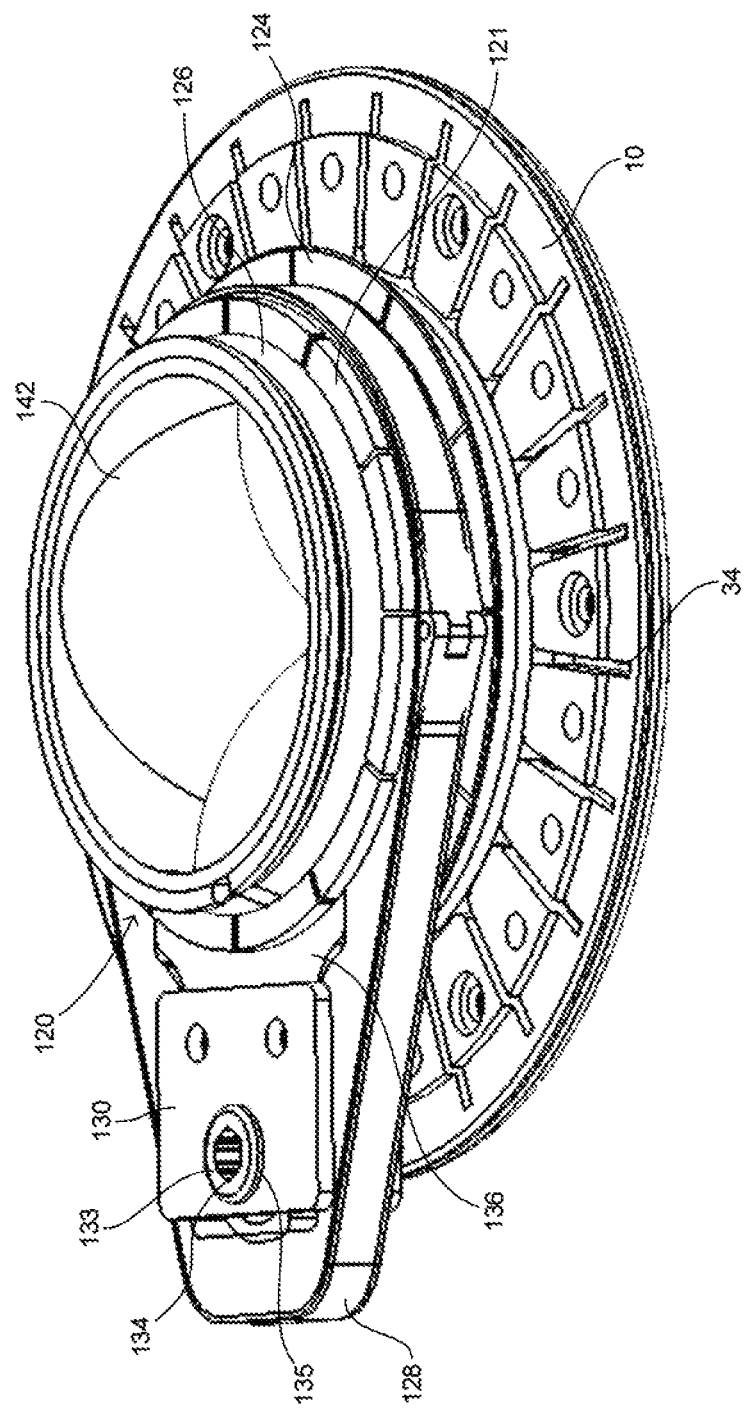
FIG. 14 illustrates a perspective view of a mounting ring in accordance with the current invention.

As best seen in FIG. 13a, an axle 190 formed from a wire is disposed in the inner channels 35a and 35c of the plate pieces 31 and 32, so that the axle is secured within the plate, between the two pieces, when the pieces are fastened together. The axle extends in a circle around the central axis 192 of the opening 33, corresponding to the circular inner channel. This circle lies in a plane transverse to the central axis 192. In the embodiment shown, the plane of the circle is perpendicular to the central axis 192 of the opening. The axle extends through the passageways 34 of the plate near the radially inward end of each passageway. Each hook 61 is disposed within one channel 34 of the plate. The axle 190 extends through the axle opening 66 of each hook, so that each hook is movably secured to the plate 10 by the axle. In the retracted position depicted in solid lines in FIG. 13a, the arm 63 of each hook 61 projects proximally from the plate, whereas the tip 64 of each hook is disposed within the associated passageway 34. In this retracted position, each hook tip 64 is at least partially within, or extends through, the associated passageway 34. The bump 67 maintains the position of the tip 64 within the passageway 34 by contacting the proximal side of the plate 10, preventing over-rotation of the hook away from the passageway. The gasket 51 is adjacent the distal surface of the plate, as best seen in FIG. 13a. The gasket 51 holds the hooks in their retracted positions.

Figure 7:
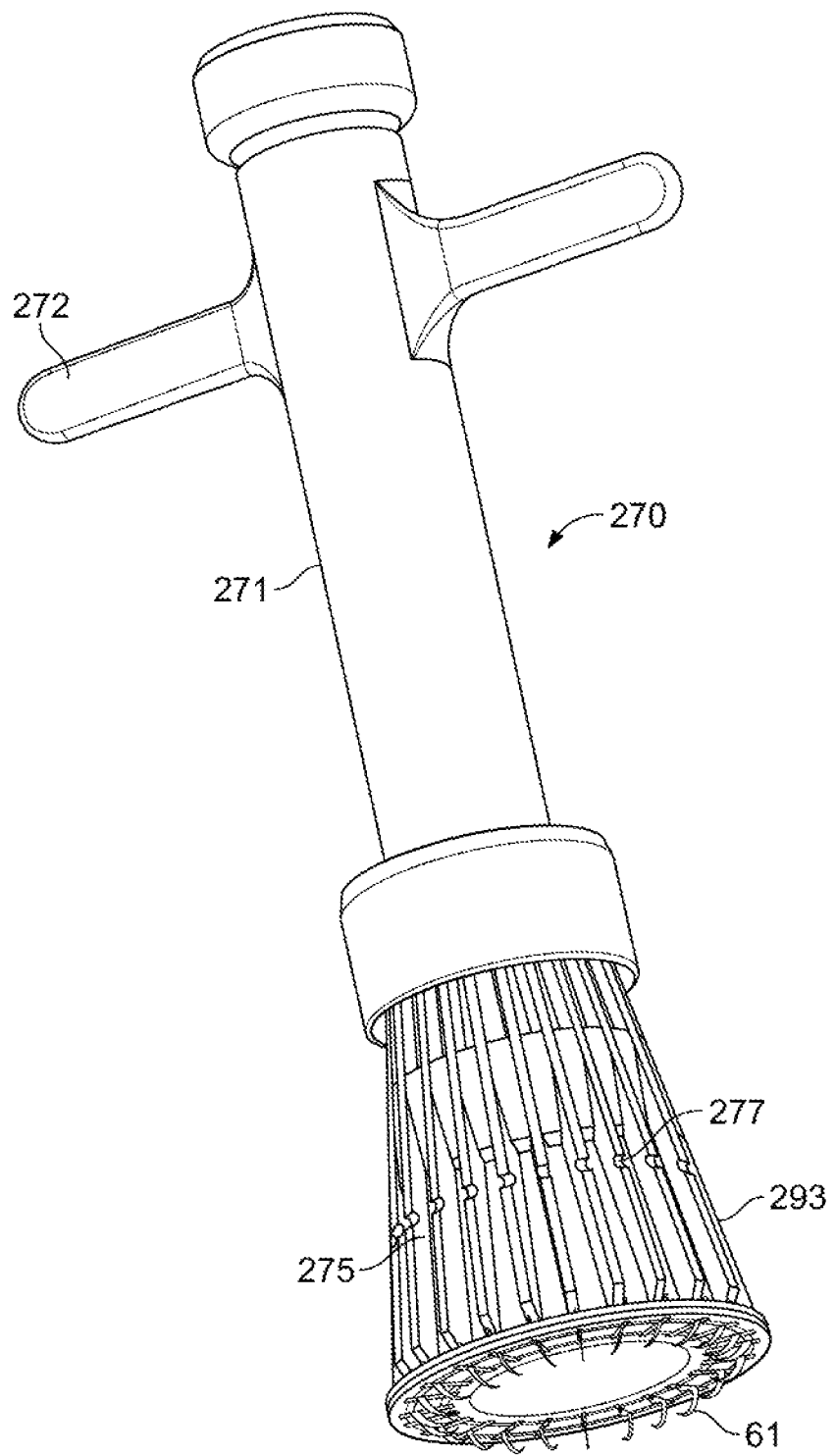
FIG. 7 illustrates a perspective view of a tool for installing the plate and anchors of FIGS. 1-6.
Figure 8:
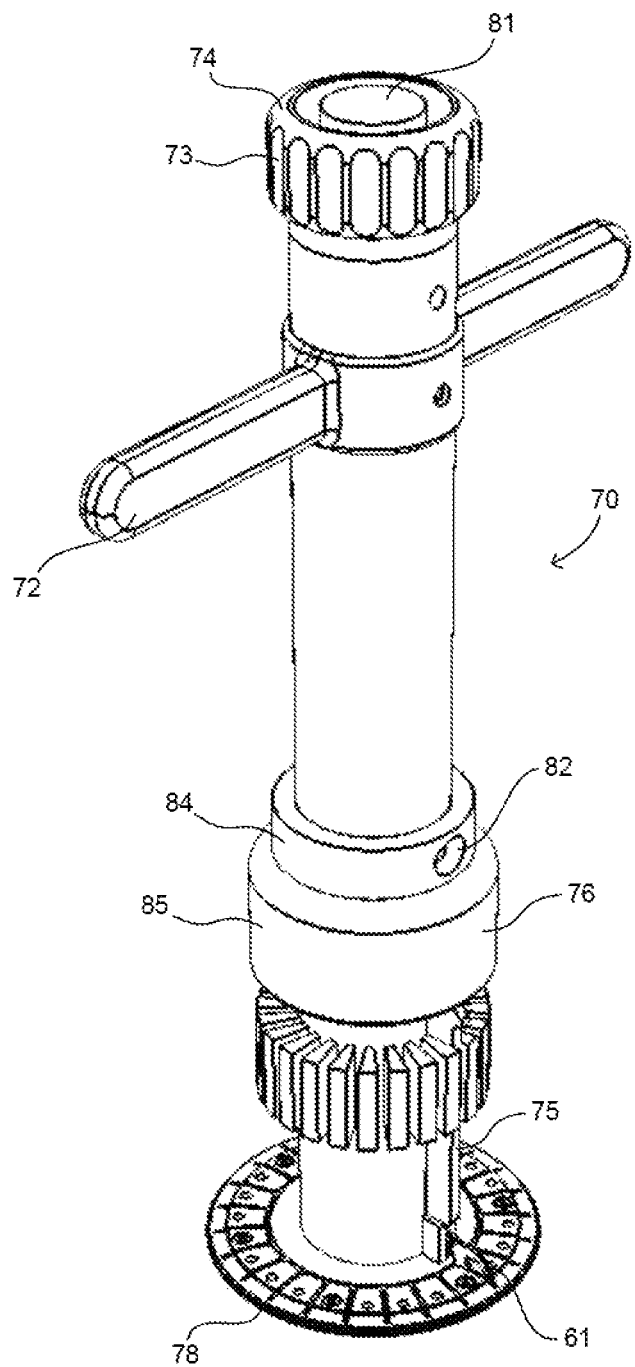
FIG. 8 illustrates a perspective view of another embodiment of a tool for installing the plate and anchors of FIGS. 1-6.
Figure 9:
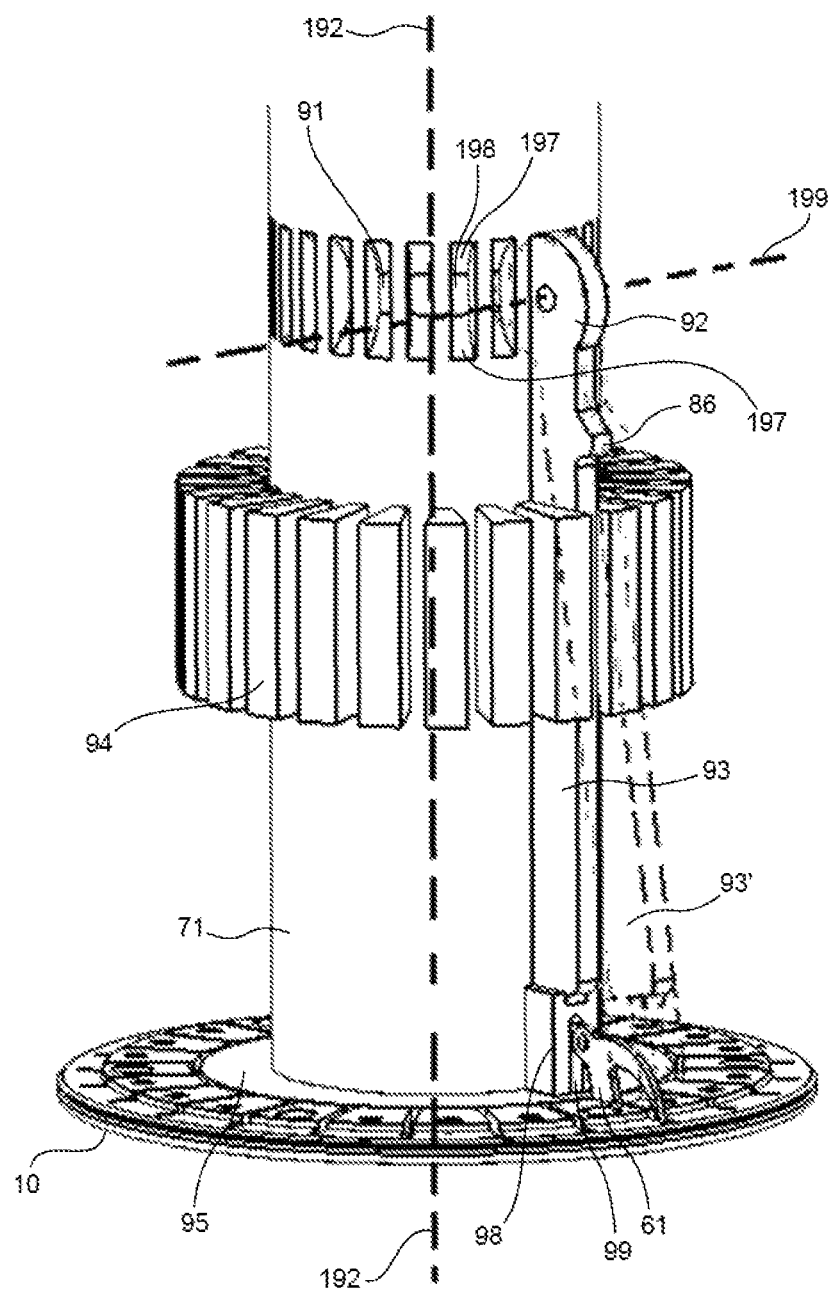
FIG. 9 illustrates a detail view of the distal end of the tool of FIG. 8.
Figure 12B:
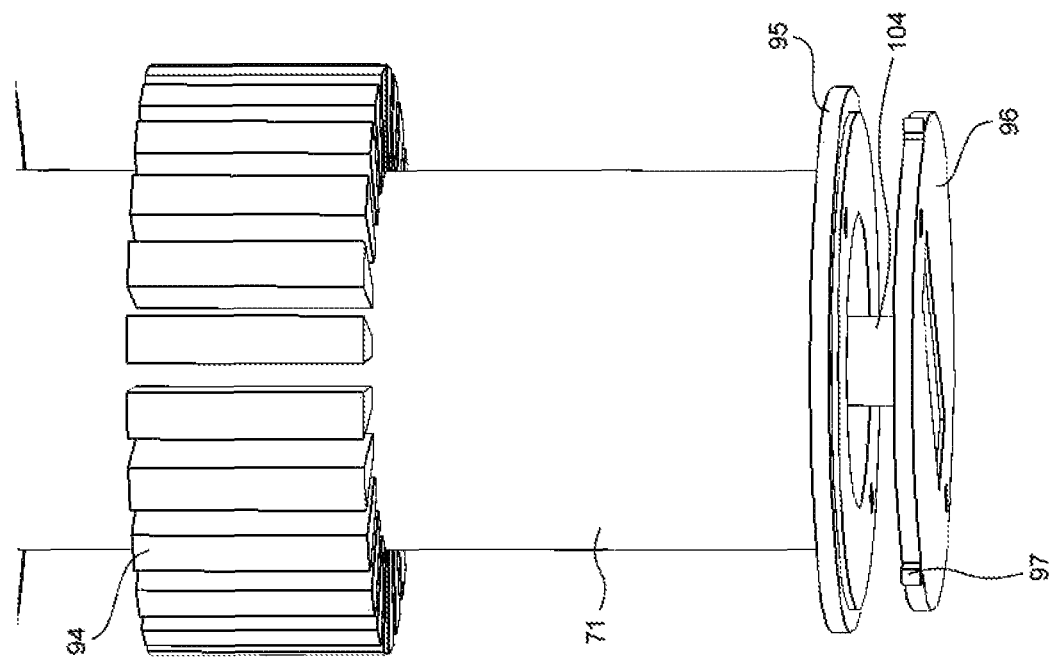
FIGS. 12a and 12b illustrate a close-up view of the distal end of the tool of FIG. 8.
Figure 12A:
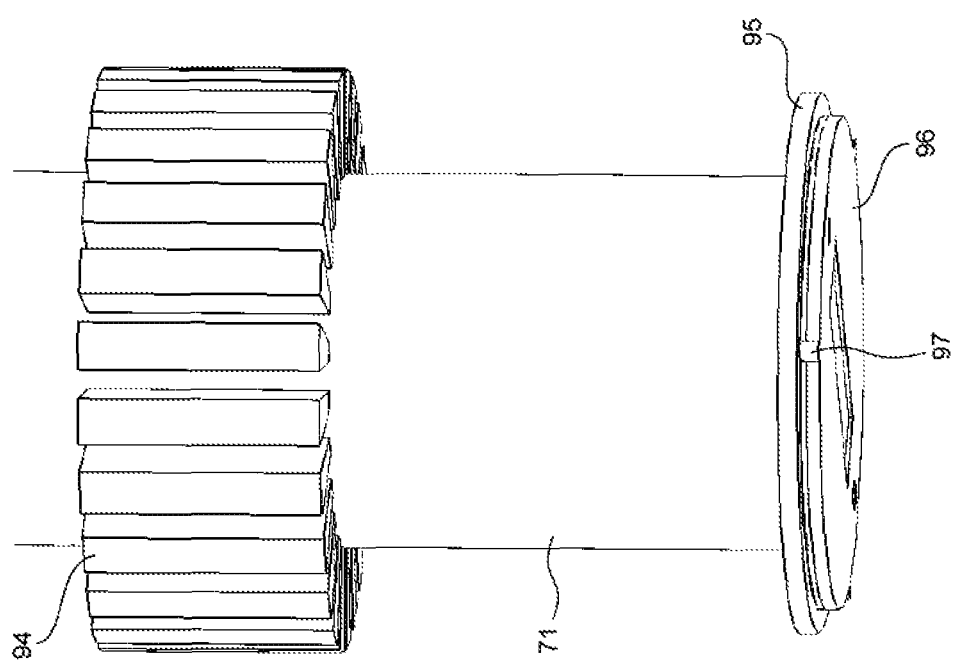

A tool 70 for deploying the hooks 61 is best shown in FIG. 7. The tool 70 has a hollow tubular body 71 with an axis 192 extending from the proximal end 74 to the distal end 78. A handle 72 extends from the body 71 transverse to the axis. The handle can be formed as an integral part of the tool (FIG. 7) or be a separate element which is secured to the tool (FIG. 8). A plurality of slots 91 (FIG. 9) extending through the wall of body 71 at locations spaced around the circumference of the body. Each slot has a pair of surfaces 197 sloping to an opening 198 where the slot is open to the interior of the body. Surfaces 197 are sectors of a circle having an axis (not shown) disposed outside of the body and extending transverse to axis 192. Ribs 94 extend from the body 71 distal to slots 91. Ribs 94 are spaced apart from one another around the circumference of body 71. The ribs have a wedge shaped cross-section to provide a consistent space between the ribs. A lip 95 (FIGS. 9 and 12) extends radially away from the body axis 192 adjacent the distal end 96 of the body 71 as best seen in FIGS. 9 and 12a.

Figure 11:
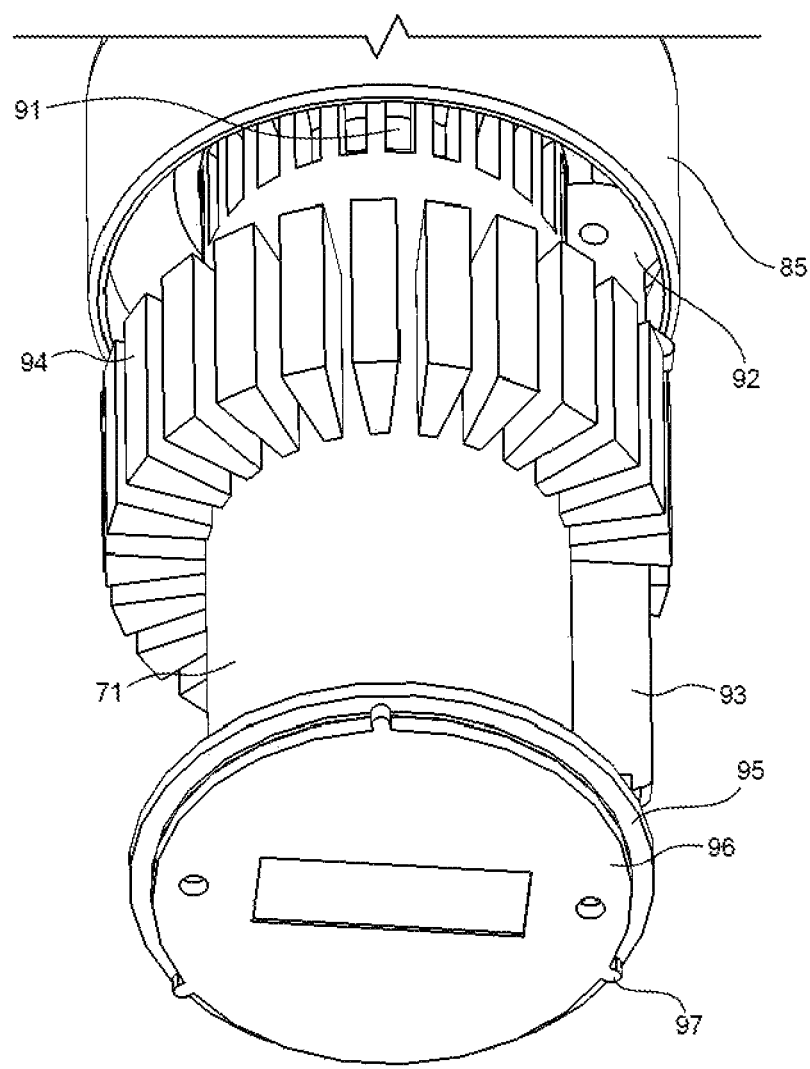
FIG. 11 illustrates a bottom perspective view of the tool of FIG. 8.

The tool 70 also includes a cage 76 (FIGS. 8 and 11) having a bell-shaped configuration. The first portion 84 of the cage closely surrounds the body 71. The second portion 85 of the cage flares out wider than the outer diameter of the body 71. As best seen in FIG. 11, second portion 85 of the cage surrounds the slots 91 of the body. The cage 76 includes an orifice 82 adapted to receive a screw or similar type of anchor to secure the cage 76 to the body 71.

Figure 10:
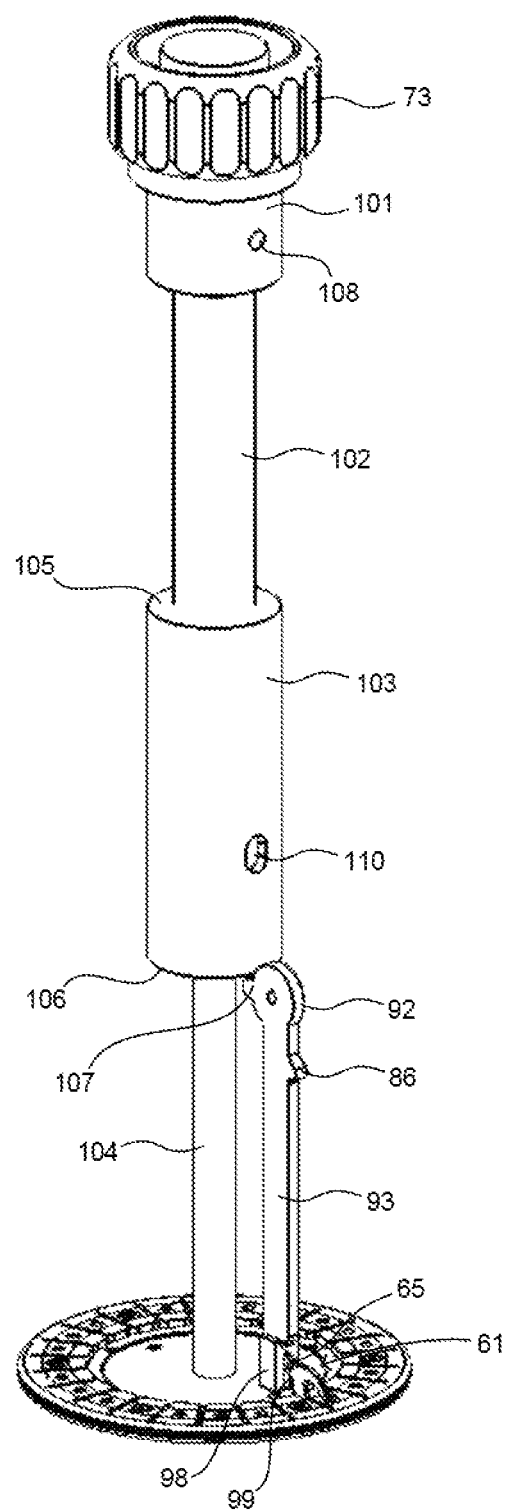
FIG. 10 illustrates a perspective view of some of the internal components of the tool of FIG. 8.

The tool also includes a knob 73 having a knurled surface as best seen in FIG. 8. The knob has an open internal cavity to receive a pushbutton 81. A shaft 102 is fixed to knob 73 and extends distally from the knob 73 as best seen in FIGS. 10 and 13. A bore is formed in the shaft 102 to receive a pushrod 104. The distal end of the shaft 102 is threaded to allow the plunger 103 to translate along the body axis as the knob 73 is rotated. The shaft 102 also has an external notch 89 to receive a retaining ring.

The tool 70 also includes an internal collar 101 which is fixed to the body 71. The collar 101 has an internal bore to receive the shaft 102.

The tool 70 also includes a plunger 103 which is configured for translational movement along the body axis. A bore extends through the plunger 103 from a proximal end 105 to a distal end 106. The proximal end 105 of the bore is sized to receive the shaft 102 and has a threaded surface matching the threads of the shaft. The distal end 106 of the bore is sized to allow a rod 104 to extend through the plunger 103. The plunger 103 has a slot 110 (FIG. 10) in its external surface. The slot 110 is sized to receive a stop (not shown) which prevents rotational movement of the plunger 103 and limits the translational movement of the plunger along the body axis. The connector which secures the cage 76 to the body 71 can also extend through the body and function as the stop for the plunger 103.

As best seen in FIGS. 8 and 11, a pushbutton 81 is exposed at the proximal end 74 of the tool 70. Rod 104 extends from the pushbutton 81 along the length of the tool 70 (FIG. 13). The distal end of the rod 104 is connected to a flange 96, best seen in FIGS. 11 and 13. As shown in FIG. 11, the lip 95 on the body 71 is slightly larger than the flange 96, although they could be of equal size. Nubs 97 extend from the perimeter of flange 96. Nubs 97 are arranged in a pattern corresponding to the pattern of the notches 42 in the plate 10 forming the bayonet lock (FIG. 4). The pushbutton 81 and rod 104 are adapted to move between a first position where the flange 96 is adjacent the lip 95 (FIG. 12a) and a second position where the flange 96 is separated from the lip 95 (FIG. 12b). Merely by way of example, the axial movement of the flange 96 between the first position and the second position may be about 0.028 inches. A spring (not shown) is positioned between the pushbutton 81 and knob 73 to bias the rod in proximal direction, towards the first position.

The tool 70 includes a plurality of fingers 93 distributed around the circumference of the tubular body 71. One finger is provided for each hook on the mounting plate. For clarity of illustration, only one of the fingers is shown in FIGS. 8-10. Each finger 93 is an elongated member having a circular head 92 at the proximal end opposite a tail 98 at the distal end. Merely by way of example, the head 92 may be about 0.375 inches in diameter. A nose 107 extends from the head 92 transverse to the direction of elongation of the finger. The finger 93 has a bulge 86 between its proximal and distal ends. The tail 98 has a groove 99 adapted to receive the protuberance 65 of a hook 61.

As shown in FIG. 9, each finger 93 is positioned along the external surface of the distal end of the body 71. In a first position depicted in solid lines in FIG. 9, each finger lies between a pair of ribs 94. The tail 98 of each finger is positioned near the proximal side of the lip 95. The head 92 is partially inserted into one of the circular slots 91 in the tool body 71. The portion of the head 92 that is not within the slot 91 remains in the space between the body 71 and the second part 85 of cage 76 (FIG. 11). Thus, the circular head 92 of each finger is confined within the associated slot 91, and bears on the circular surfaces 197 of the slot (FIG. 9). Thus, each finger is mounted to the body 71 for pivoting motion around an axis 199 transverse to the axis 192 of body 71. The nose 107 of each finger projects into the interior of body 71 just distal to plunger 103. Thus, rotation of knob 73 to drive plunger 103 in the distal direction will push the noses of the fingers distally and thus will pivot each finger 93 from the first position depicted in solid lines in FIGS. 9 and 13a to the second position depicted in broken lines at 93'.

Figure 15:
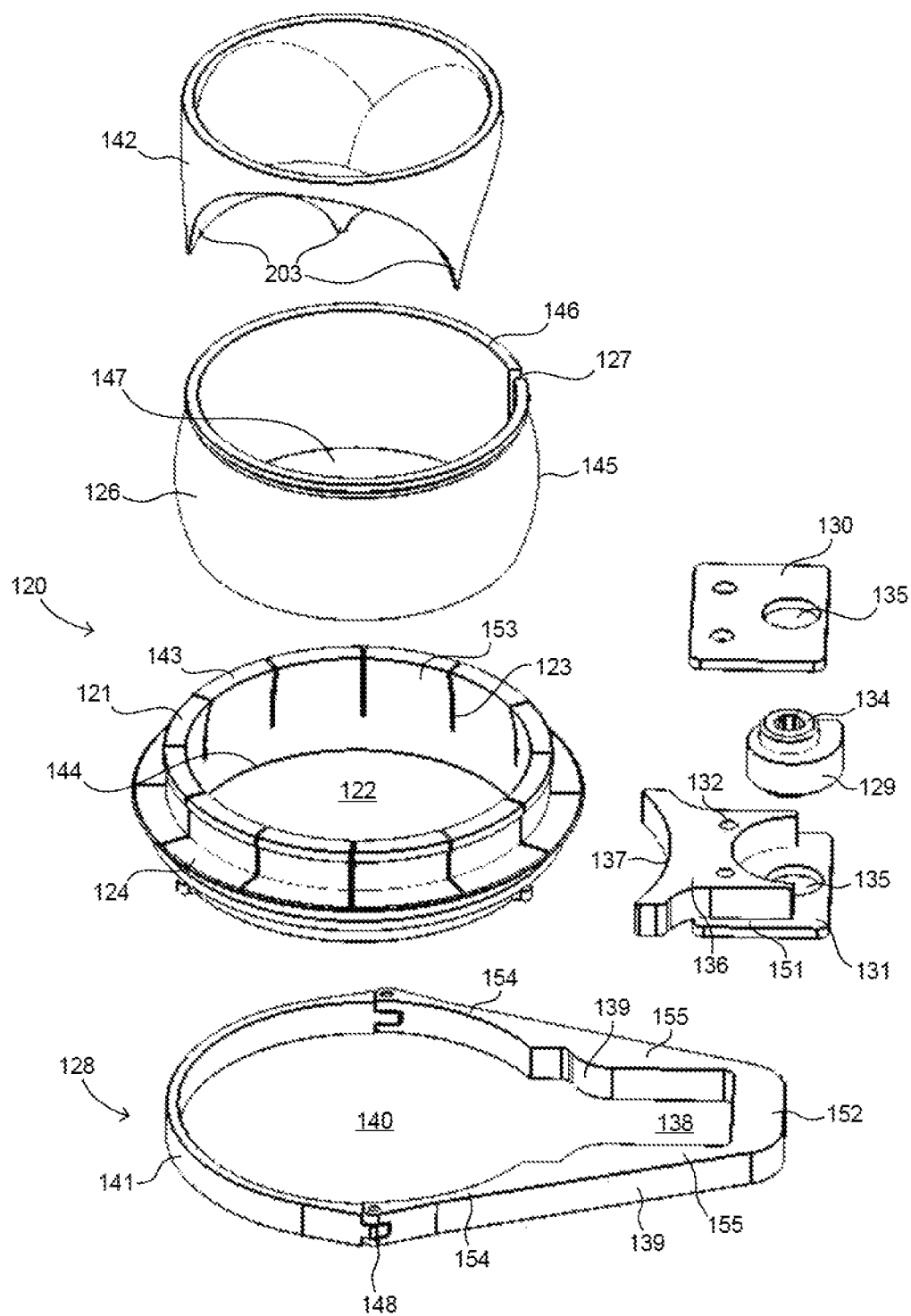
FIG. 15 illustrates an exploded view of the adaptor of FIG. 14.
Figure 18:
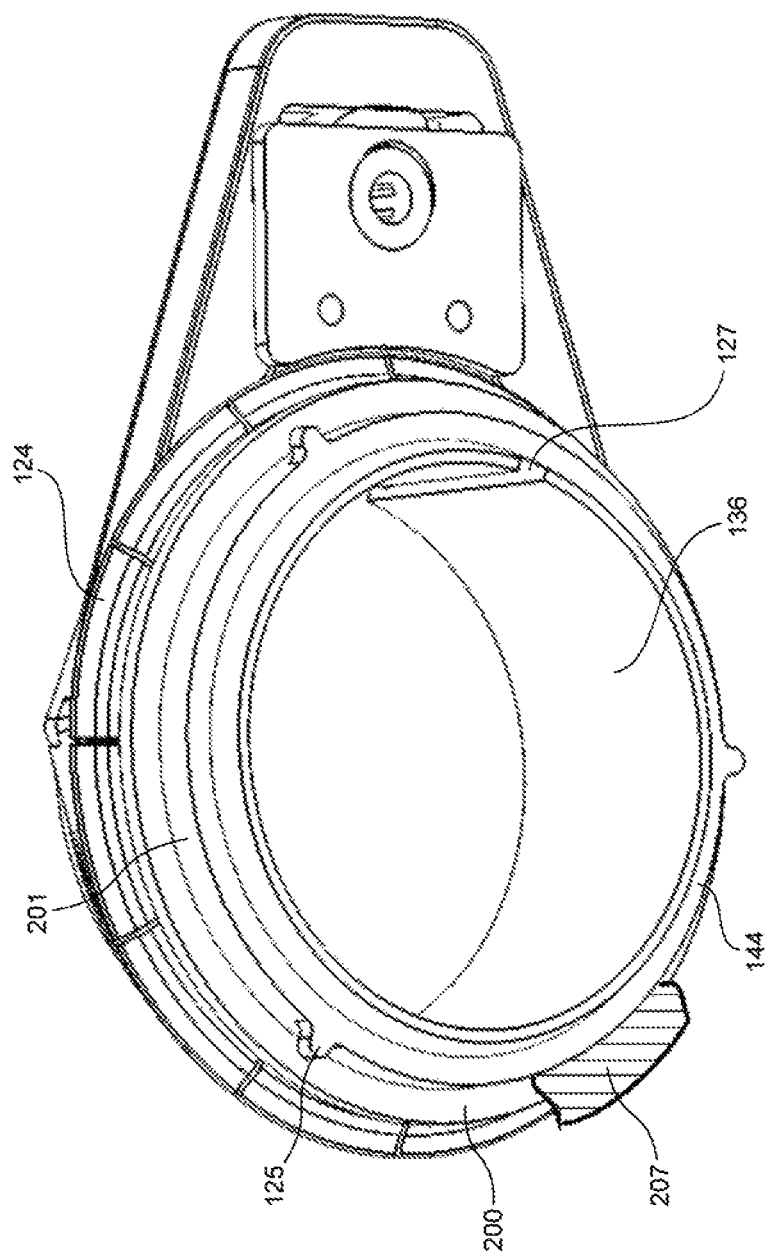
FIG. 18 illustrates a bottom perspective view of the adaptor of FIG. 14.

The kit further includes an adaptor shown in FIGS. 14-18. In the embodiment shown, the adaptor includes an annular wall 121 (FIG. 15) and a gimbal 126. As best seen in FIG. 15, the annular wall 121 has a plurality of slits 123 extending from a proximal side 143 toward a distal side 144. The slits 123 separate the proximal portion of the annular wall 121 into tabs 153. The interior of the annular wall defines an opening 122 with a spherical interior surface. The annular wall 121 can move between a first state where the slits 123 separate the tabs 153 by an initial distance and a second state where the slits 123 separate the tabs 153 by a reduced distance, so as to constrict opening 122. A rim 124 extends from the annular wall 121. The rim 124 provides a shelf for a clamp 128. The annular wall includes a distal section defining a distal-facing surface 200 (FIG. 18) and a collar 201 disposed distal to surface 200. Collar 201 has nubs 125 extending from its distal end 144. The nubs 125 are configured to engage the bayonet locking features of the plate to secure the annular wall 121 to the plate 10. A compressible gasket 207 may be positioned between the distal-facing surface 200 and nubs 125. Only a small portion of gasket 207 is depicted in FIG. 18 for clarity of illustration; the gasket preferably extends entirely around the collar 201.

The gimbal 126 is adapted to fit within the opening 122 in the annular wall 121. The gimbal 126 has a semi-spherical outer contour 145, an interior bore 147 and a relief 127 extending through the wall of the gimbal. Gimbal 126 is received within the opening 122 of the annular ring, so that the gimbal can pivot slightly to tilt the axis of bore 147 relative to the annular ring. A lip 146 is adjacent the proximal end of the gimbal 126 which limits the range of rotation of the gimbal. The relief 127 allows the gimbal to expand and contract beyond its resting configuration.

A tri-leaflet valve 142 formed from a resilient, biocompatible material is provided as shown in FIG. 15 within gimbal 126. The leaves 203 of the valve normally abut one another to substantially occlude the bore 147 of the gimbal. However, when a solid object is inserted through the bore of the gimbal, the leaves of the valve will move to allow passage of the object.

Figure 16:
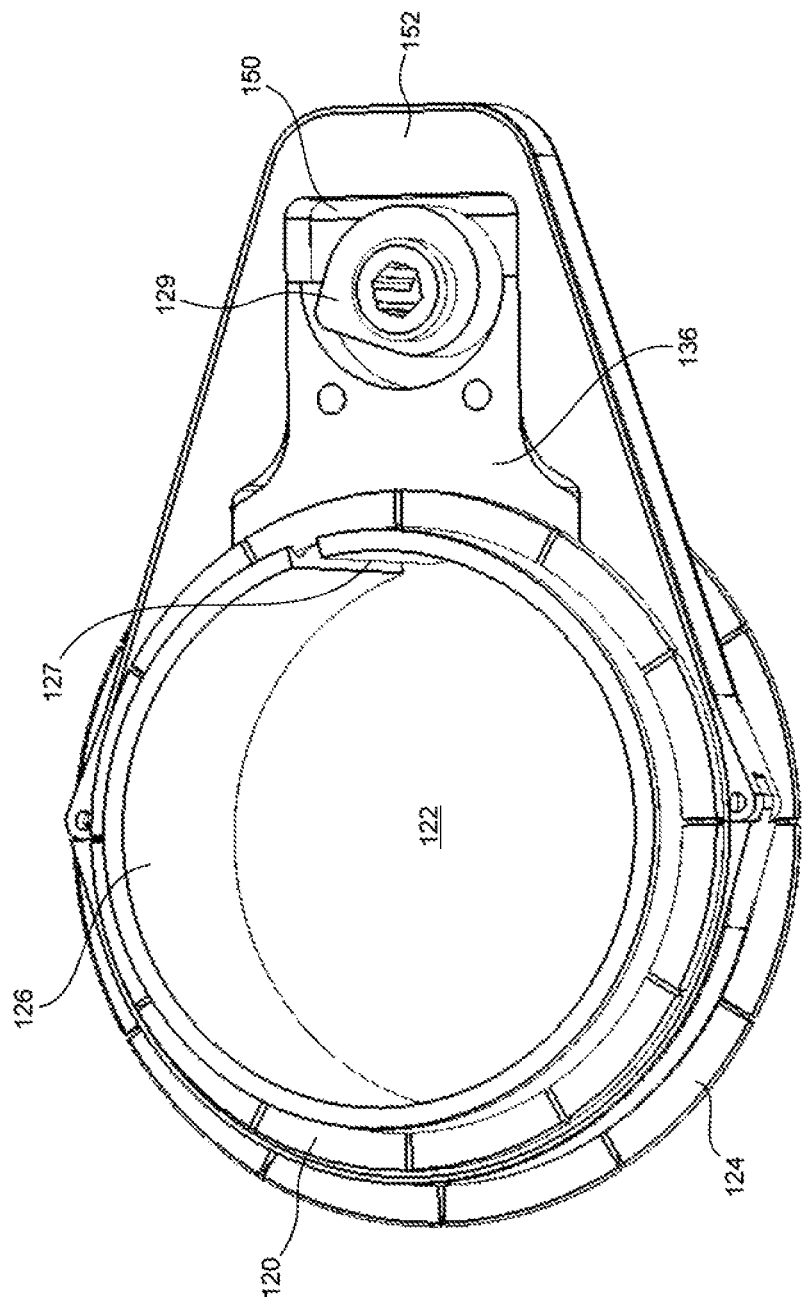
FIG. 16 illustrates a perspective view showing the inner components of the clamp of FIG. 14.
Figure 17:
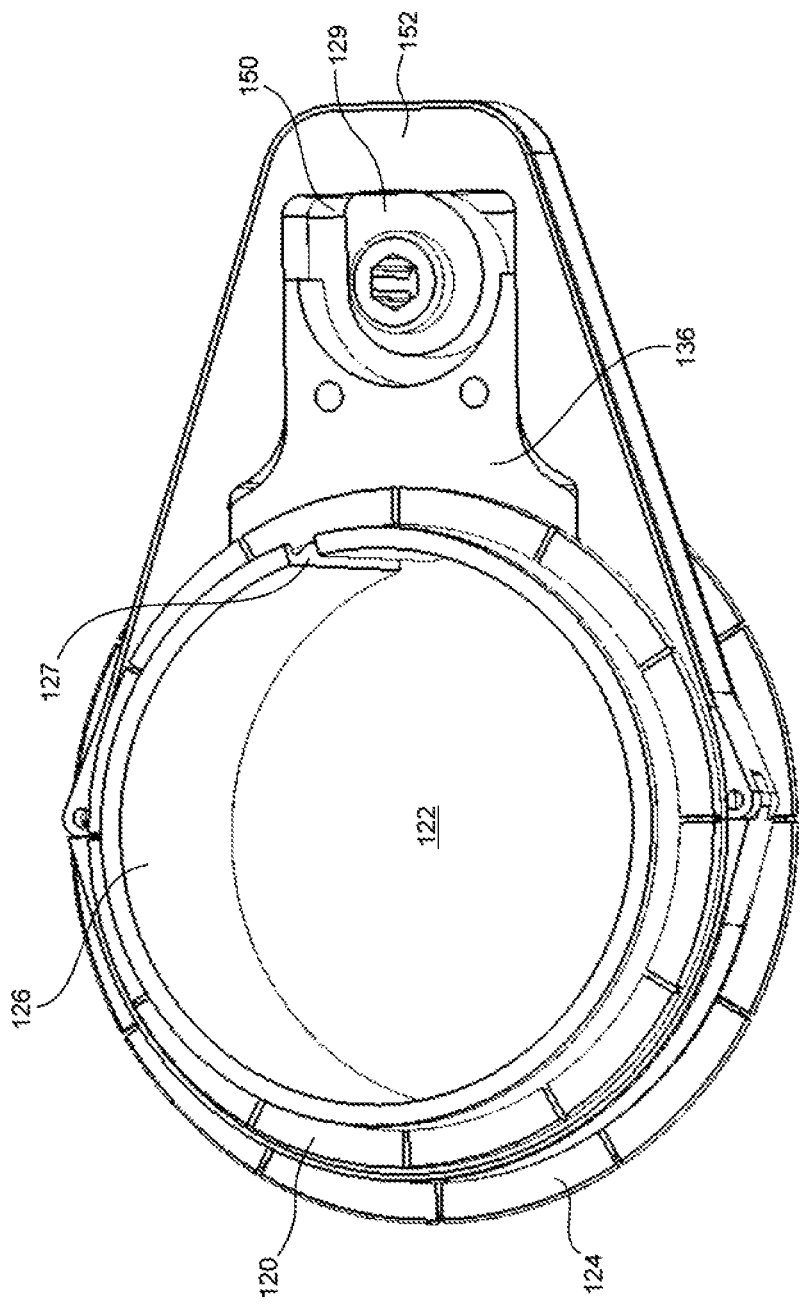
FIG. 17 illustrates a perspective view showing the inner components of the clamp of FIG. 14.

A clamp 128 is provided with legs 139 and a body 141. The body 141 is semi-circular member with a radius generally equal to or greater than the exterior radius of the slotted section of annular wall 121. The legs 139 have a first portion 154 with an internal arcuate surface with a radius similar to that of the body 141. The legs 139 are secured to the body 141 by a hinge 148. Once connected, the clamp 128 forms a void 140 to receive the slotted section of annular wall 121. The legs 139 each include a second portion 155 which is connected to a leg connector 152 and define a receiving area 138 for a brake 136. The leg connector 152 includes a generally flat actuation surface 150, as best seen in FIG. 16.

The brake 136 has a surface 137 with a semi-circular contour with a radius similar to that of the body 141. The brake 136 has a cutout 156 to provide a space for an actuator 129. The brake 136 is fixed to a top plate 130 and a bottom plate 131. The plates 130, 131 have a hub bearing 135 which receives and permits rotational movement of a cam 129. The plates 130, 131 extend beyond the perimeter of the brake 136 to form ledges 151. The ledges 151 overlap the legs 139 when the brake 136 is placed within the brake receiver 138. Thus, the brake 136 is slidably mounted in brake receiver 138 for motion towards and away from body 141. The cam 129 has a head 134 adapted to receive a wrench. Using the wrench, cam 129 can be rotated to drive brake 129 towards body 141, and thus constrict void 140. This action also constricts the slotted portion of annular wall 121 and constricts gimbal 126. The particular clamp depicted is merely exemplary. Other types of clamps, such as those disclosed in U.S. Provisional Patent Application 62/013,156 also can be used.

One method of attaching the mounting ring to a heart begins with securing the plate 10 to the tool 70. At this stage, the fingers of the tool 70 are in the first position 93 shown in solid lines, and the hooks 61 are in the retracted position relative to the plate. The nubs 97 (FIG. 11) are aligned with the notches 42 (FIG. 4) and moved through the plate from the proximal side 38 to the distal side 39 of the plate 10. The flange 96 is then rotated relative to the plate 10 to move nubs 97 along the ramps 43 and into the pits 44. It is believed that pressing the pushbutton 81 when rotating the tool 70 relative to the plate 10 may make it easier to advance the numbs 97 along the ramps 43 and into the pits 44. Once the nubs 97 are aligned with the pits 44, the pushbutton 81 is released and the flange 96 moves proximally, thus allowing the nubs to move proximally into the pits. In this condition, the tool 70 is securely coupled to the plate 10, with the plate clamped between flanges 95 and 96 of the tool, and with the plate locked against rotation relative to the tool by the engaged nubs 97. The central axis 192 of tool body 71 is coaxial with the central axis 13 of the opening in plate 10. In some embodiments, the plate and tool may be secured to each other before being provided to the user (for example, by the manufacturer).

The distal side 39 of the plate 10 is then placed adjacent an external wall of the heart with the hooks 61 in the retracted position. The knob 73 on the tool is rotated and the threaded connection between the knob 73 and the plunger 103 causes translational movement of the plunger 103 in the distal direction. As the plunger 103 moves, it contacts the nose 107 of each finger 93, causing the fingers to move from the first position shown in solid lines in FIG. 9 toward the second position shown in broken lines at 93'. The head 92 of each finger is retained in the slots 91 by the internal surface of the second portion 85 of the cage 76. The tail 98 of each finger moves away from the body 71 as the finger 93 pivots toward the second position. The ribs 94 prevent misalignment of the fingers 93 during rotation. The protuberance 65 of each hook 61 is adjacent to the tail 98 of a finger and within groove 99. As the finger 93 pivots, the tail 98 of each finger moves outwardly away from the central axis of the body, so that the tail of each finger moves from the first position illustrated in solid lines in FIG. 13a to the second position illustrated in broken lines at 98'. The tail 98 of the finger pushes the protuberance 65 outwardly away from the opening 33 in the plate 10. As best seen in 13a the hook 61 rotates about the axle 190 as the protuberance 65 is moved by the tail 98, so that the hook 61 swings from the retracted position depicted in solid lines to the advanced position shown at 61'. Because the tip 64 of each hook is already disposed within a passageway or slot 34 of the plate 10 when the hook is in the retracted position, the hooks are continuously guided by the walls of the passageways in the plate as they move from the retracted position to the advanced position. The plate thus helps to prevent twisting or distortion of the hooks, and assures that each hook remains substantially in its original plane as it is advanced. The hooks 61 pierce the gasket 51 as they move from the retracted position to the advanced position.

The point 64 of each hook initially moves distally, and then moves both distally and inwardly toward the central axis 192, and finally begins to move inwardly and proximally as it approaches the advanced position. All of the hooks move simultaneously. The tissue of the heart is pulled toward the distal side of the plate 10 as the hooks 61 are inserted. The gasket 51 is compressed by the heart and the plate 10 as the two are drawn together, thereby creating a seal between them. As the finger 93 continues to rotate, the bulge 86 on each finger contacts the distal end of the cage 76 to prevent over-rotation of the fingers 93. The stop protruding through the cage 76, through the body 71, and into the orifice 82 on the plunger also stops the movement of the plunger 103 in the distal direction. Further, the threads of the shaft 102 and plunger 103 are configured to provide limited translational movement of the shaft relative to the collar. The hooks 61 are in the advanced position when the fingers 93 have reached their maximum rotation as best shown in FIG. 7.

The knob 73 can then be rotated in the opposite direction to move the shaft 102 back to its original position. The fingers 93 are also free to move back to their first position. The fingers may be biased toward the first position by one or more resilient elements as, for example, an elastic band such as an O-ring (not shown) encircling the fingers. In other embodiments, the shaft could be coupled to the plunger and each nose could be secured to the plunger such that when the knob is rotated in the direction opposite to that for deployment, the plunger and fingers are also returned to their original positions.

To remove the tool 70 from the plate 10, the pushbutton 81 is pressed, causing translational movement of the rod 104 along the axis of the tool 70. The nubs 97 exit the pits 44 as the flange 96 is moved distally relative to the plate 10. The tool 70 is then rotated to move the nubs 97 along the ramps 43 and into alignment with the notches 42. The tool 70 is retracted from the plate 10, so that nubs 97 move from the distal side 39 to the proximal side 38 of the plate 10 through the notches. The tool 70 is then removed from the plate 10, leaving the plate securely fastened to the exterior of the heart.

The adaptor 120 can be secured to the plate 10 after the plate 10 is secured to heart and the tool 70 is removed. The assembled adaptor 120 is placed adjacent the proximal side 38 of the plate 10. The nubs 125 of the annular wall 121 are secured to the bayonet lock feature of the plate by passing nubs 125 distally through slots 42 and rotating the adaptor until the nubs engage pits 44. The gasket 51, which is compressed between the plate 10 and the heart, also provides a spring force against the nubs 125 to lock the nubs 125 in the pits 144. In this condition, the adaptor overlies at least part of the proximal surface 38 of the plate, with the distal facing surface 200 (FIG. 18) of the adaptor confronting the proximal surface of the plate. Gasket 207 (FIG. 18) is compressed between surface 200 of the adaptor and the plate to bias the adaptor proximally relative to the plate. Gasket 207 thus maintains more secure engagement of the nubs 125 and the pits 44, and also forms a seal between the adaptor and the plate. The adaptor blocks backward rotation of the hooks, from the advanced position toward the retracted position.

The foregoing steps can be completed in far less time than required for installation of a conventional mounting ring. This reduces the time the patient must be kept under anesthesia. Such reduction is particularly valuable for very sick patients who require installation of a VAD. Moreover, the foregoing steps can be performed using a relatively narrow surgical access to the heart.

After installation of the plate and adapter, a coring tool can then be used to cut a hole in the exterior wall of the heart. One such coring tool is described in U.S. Patent Publication No. 2009/0012552, the disclosure of which is hereby incorporated herein. The coring tool can be advanced to the heart wall through the valve 142 in the adaptor. In some embodiments, the coring device may be used to transport the adaptor to the plate. The adaptor can be positioned about the outside of the coring tool. Although the present invention is not limited by any theory of operation, it is believed that using the coring tool to deliver the adaptor to the plate may save time during an operation by aligning both the coring tool and the adaptor with the opening in the plate at the same time.

After the coring tool cuts a hole in the heart, the valve 142 substantially prevents the exit of blood through the hole. It is not necessary for the valve to completely eliminate blood loss. A device such as a VAD or an inlet tube connected to a VAD (not shown) is inserted into the bore 205 of gimbal 126 through valve 142. The clamp 128 is then tightened so as to compress the annular ring and gimbal and thus lock the device in place relative to the heart. Before tightening the clamp, the clamp can be rotated about the annular wall 121 until it is in a desired orientation with respect to the annular wall when the clamp is in the first configuration. An instrument is then coupled to the head 134 to manipulate the cam 129. The instrument can be inserted for use through the same surgical accessway used to install the plate and adapter. It is believed that this orientation eliminates the need for a separate, or enlarged, accessway employed in traditional surgeries to implant a mounting ring.

Figure 19A:
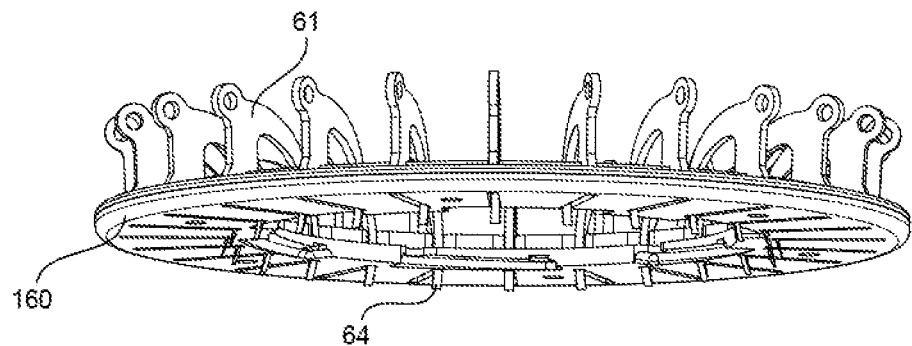
FIGS. 19a and 19b illustrate a perspective view of another embodiment of a plate with hooks in accordance with the current invention.
Figure 19B:
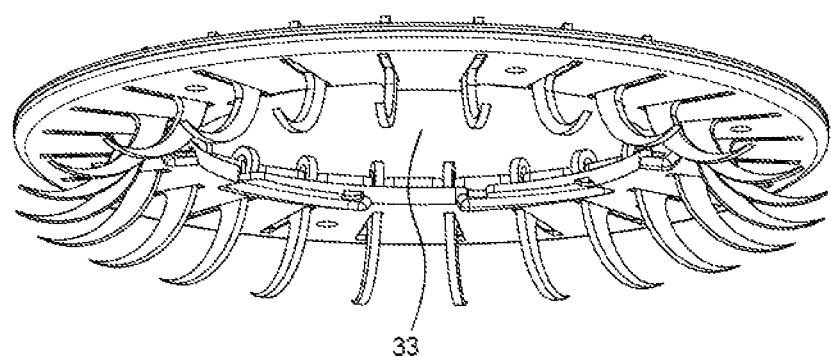

Numerous variations and combinations of the features discussed herein can be employed. For example, a mounting plate 160 in accordance with another embodiment of the current invention is shown in FIGS. 19a and 19b. The hooks 61 are coupled to the plate 160 by an axle in the outer channel 35b, best seen in FIG. 3. The tool is arranged to drive the arms 62 and protuberances 65 inwardly, toward the central axis 13 of the plate. In this arrangement, the tips 64 of the hooks move distally and then move outwardly, away from the central axis, as the hooks move from their retracted positions (FIG. 19a) to their advanced positions (FIG. 19b). The tips 64 extend slightly through the distal side of the plate 160 in this embodiment when the hooks 61 are in the retracted position as shown in FIG. 19a. The plate 160 is similar to that previously described but the tips 64 swing away from the opening 33 as the hooks 61 are rotated from the first position to the second position (FIG. 19b). A tool (not shown) for use with this plate may have fingers arranged to move inwardly toward the central axis of the tool, rather than outwardly, during the installation process.

Figure 22:
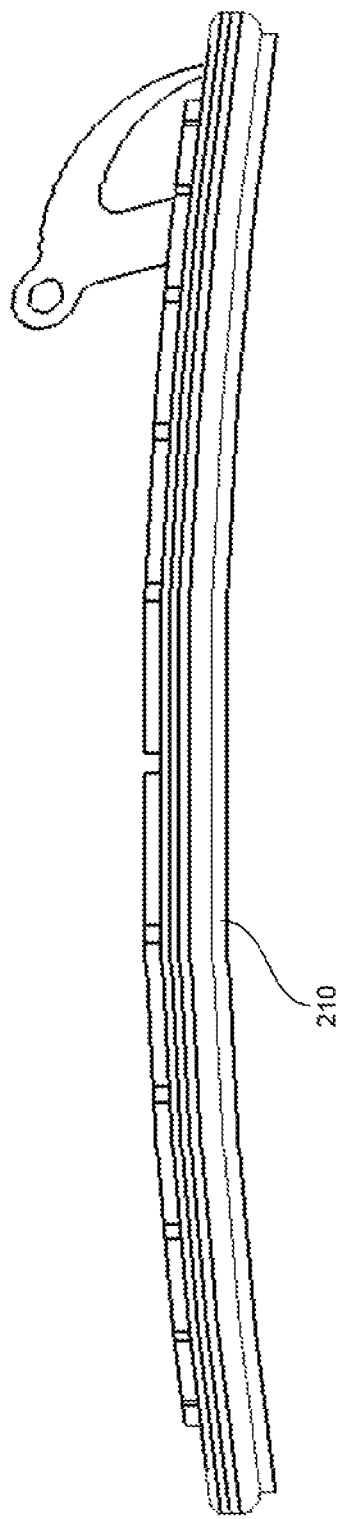
FIG. 22 illustrates another embodiment of a plate in accordance with the current invention.

Another embodiment of a plate 210 is best seen in FIG. 22. As shown, the distal surface 239 of the plate 210 is curved so that it is generally concave. The degree of curvature can be selected to follow the contour of the heart at the site where the plate will be attached. The plate profile shape could also be conical, hemispherical, cup shaped, etc.

In the embodiments discussed above, the adaptor which holds the VAD is provided as a separate element which is installed on the mounting plate after the mounting plate is secured to the heart. This is advantageous in that mounting tool can be accommodated in the space on the proximal side of the mounting plate which is later occupied by the adaptor. However, in other embodiments, part or all of the adaptor may be integral with the mounting plate or permanently connected to the mounting plate before use. In those embodiments where the adaptor is directly connected to the VAD, the process described for attaching the annular wall can be omitted. Conversely, the VAD or other device to be mounted may be provided with features such as nubs which engage the mounting plate directly, and the adaptor may be omitted.

Although the knob has been described as the element that provides translational movement of the plunger, other actuating elements could also be provided to perform this action (e.g. a slideable actuator, a pushbutton, a lever). The linkage between the actuating element of the tool and the fingers need not incorporate the plunger arrangement discussed above. Other mechanical, hydraulic, pneumatic or electromechanical devices can be used to move the anchors. Further, the tool could be adapted to advance the anchors sequentially, either one at a time or several groups of anchors at a time, rather than simultaneously.

Another embodiment of a tool 270 is shown in FIG. 7. As shown, the handle 272 is formed as part of the body 271. In addition, the fingers 293 have a ridge 277 to accept an O-ring (not shown). The O-ring may be an elastic material to bias the fingers toward the first position.

Figure 20A:
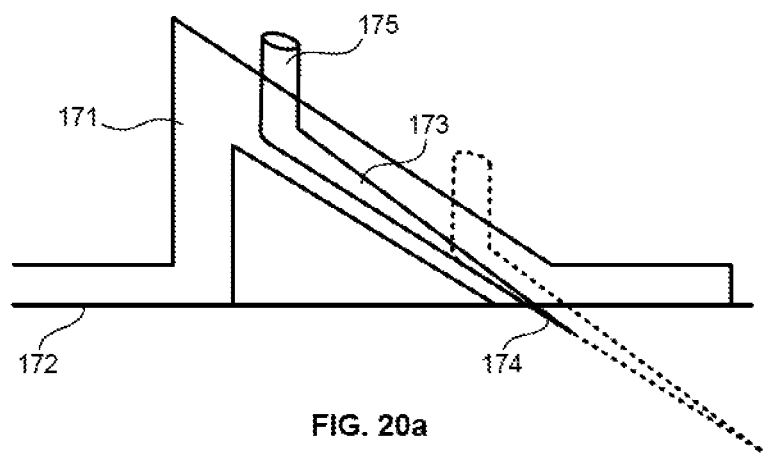
FIG. 20a illustrates another embodiment of a plate with anchors in accordance with the current invention.
Figure 20B:
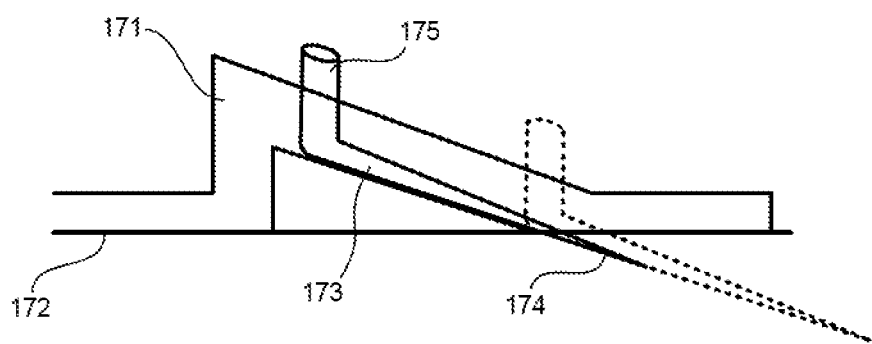
FIG. 20b illustrates another embodiment of a plate with anchors in accordance with the current invention.

Another embodiment of an anchor in accordance with the current invention is shown in FIGS. 20*a* and 20*b*. In this embodiment, the anchors are pins rather than hooks, and the pins slide, rather than rotate, relative to the plate. As shown, a housing 171 extends above the plate 172. The plate 172 can have a similar configuration to that previously described with a housing 171 positioned above each passageway (not shown). The passageway extends into the housing 171 at an oblique angle to the plate 172. Each pin 173 moves within the passageway from a retracted position (solid line) to an advanced position (broken line) where the pin extends distally into the heart. Similarly to previously discussed anchors, the pin 173 has a tip 174 which is positioned within the passageway or extends distally from the plate 172 in the retracted position. A tab 175 protrudes beyond the housing 171 which can be used to move the pin 40 between the first and second position. The anchors could also have barbs on the tips to maintain the anchors in the deployed position.

FIG. 20*b* shows another configuration of the housing 171 depicted in FIG. 20*a*. This configuration provides a different angle of entry as the pin 173 moves from the retracted position (solid line) to the advanced position (broken line). The tool can also be adapted to insert the pin anchors described in this embodiment.

Figure 21A:
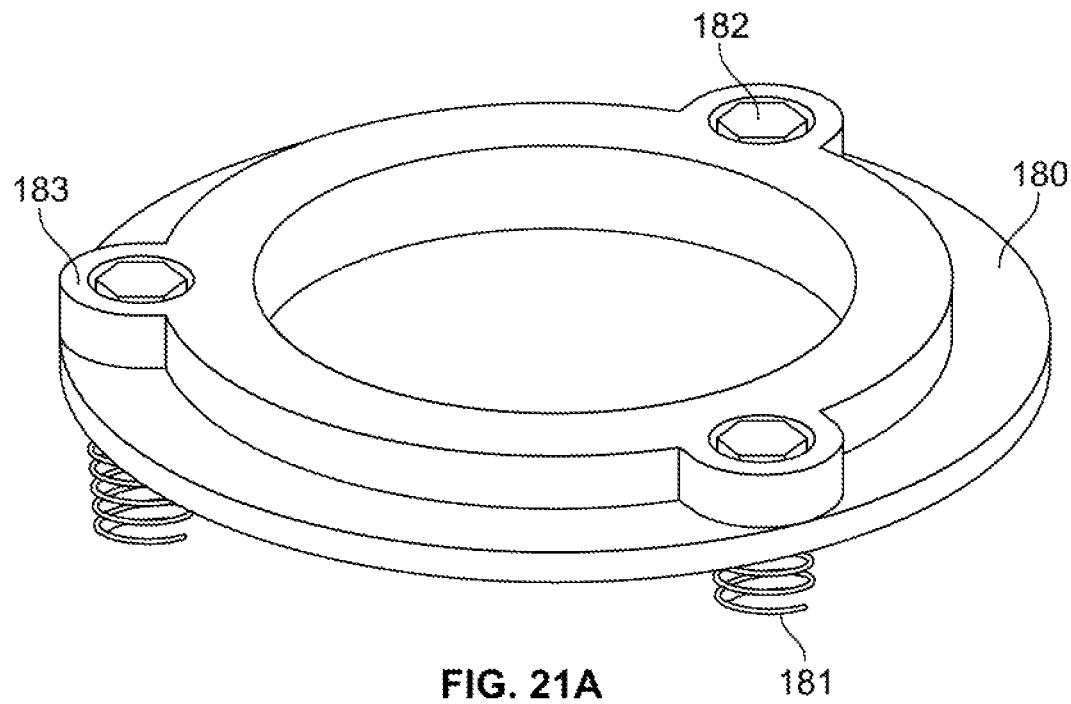
FIG. 21a illustrates a perspective view of another embodiment of a plate with anchors in accordance with the current invention.
Figure 21B:
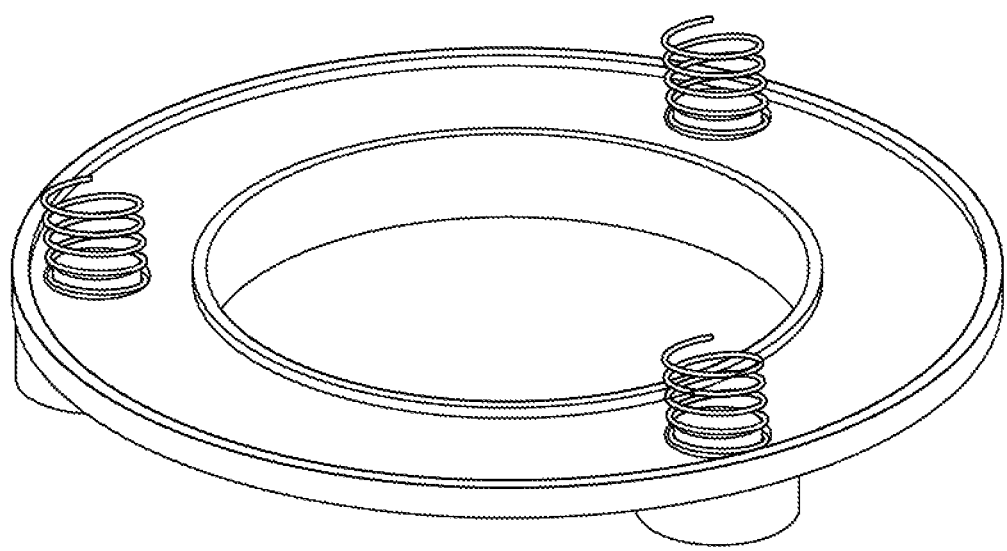

A plate and anchors in accordance with another embodiment of the current invention is shown in FIGS. 21*a* and 21*b*. In this embodiment, helical anchors 181 are used to secure a plate 180 to tissue. A housing 183 protrudes from the proximal side of the plate 180 and is configured to receive a helical anchor 181 as shown in FIG. 21*a*. The anchors are disposed in passageways extending through the housing and plate 180. The housing may be a unitary element or separate elements associated with each anchor. The helical anchor 181 has a head 182 adapted to be engaged by an insertion tool to rotate the anchor. Each head 182 can be rotated about an axis generally parallel to the proximal-to-distal axis defined by the opening 184. This allows the anchors to be inserted and tightened through the same surgical accessway used to install the plate 180.

In the embodiments discussed above, the anchors are arranged generally along a circle surrounding the central axis of the plate. However, the anchors may be disposed in other arrangements as, for example in rows or along sides of a square or other polygon.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A mounting ring kit comprising:
   a plate having a proximal side, a distal side adapted to be placed against an exterior surface of a heart, an opening extending through the plate from the proximal side to the distal side, and a plurality of passageways extending through the plate from the proximal side to the distal side;
   a plurality of rigid anchors disposed at least partially within the plurality of passageways;
   a sealing ring disposed against the distal side of the plate and extending around the opening;
   the plurality of rigid anchors being movable from a retracted position towards an advanced position in which the plurality of rigid anchors project from the distal side of the plate; and
   an adaptor coupled to the proximal side of the plate and extending around the opening to overlie the plurality of rigid anchors in the advanced position, the adaptor including a proximal side, a distal side opposite the proximal side, and a midportion therebetween, the midportion having an annular wall defining an aperture including a gimbal disposed therein and a rim extending transverse to the annular wall, surrounding the aperture, and defining a shelf; and
   a clamp disposed on the shelf of the rim.

2. The mounting ring kit of claim 1, further comprising a plurality of housings on the proximal side of the plate aligned with the plurality of passageways.

3. The mounting ring kit of claim 2, wherein the opening defines a proximal to-distal axis, the passageways extend through the housings and are oblique to the axis.

4. The mounting ring kit of claim 1, wherein the opening defines a proximal to-distal axis and wherein the anchors are mounted to the plate for pivoting motion about rotational axes transverse to the proximal-to-distal axis.

5. The mounting ring kit of claim 4, wherein the rotational axes are tangent to a circle encircling the proximal-to-distal axis.

6. The mounting ring kit of claim 1, further comprising a locking element to lock the anchors in position.

7. The mounting ring kit of claim 1, wherein each of the plurality of rigid anchors is one of a screw, hook, or pin.

8. The mounting ring kit of claim 1, wherein the anchors project from the proximal side of the plate when the anchors are in the retracted position.

9. The mounting ring kit of claim 1, wherein the anchors are adapted to pull tissue of the heart to the distal side of the plate.

10. The mounting ring kit of claim 1, wherein the sealing ring is made of a compressible material that is configured to provide a seal between the exterior surface of the heart and the plate.

11. The mounting ring kit of claim 1, wherein the annular wall is detachable from the plate.

12. The mounting ring kit of claim 1, further comprising a tool for moving the anchors from the retracted position to the advanced position.

13. A kit comprising:
   a plate having a proximal side, a distal side adapted to be placed against an exterior surface of a heart, an opening extending through the plate from the proximal side to the distal side, and a plurality of passageways extending through the plate from the proximal side to the distal side;
a plurality of rigid anchors disposed at least partially within the plurality of passageways;
a sealing ring disposed against the distal side of the plate and extending around the opening, the plurality of rigid anchors movable from a retracted position towards an advanced position in which the plurality of rigid anchors project from the distal side of the plate;
an adaptor coupled to the proximal side of the plate and extending around the opening to overlie the plurality of rigid anchors in the advanced position, the adaptor including a proximal side, a distal side opposite the proximal side, and a midportion therebetween, the midportion having an annular wall defining an aperture including a gimbal disposed therein and a rim extending transverse to the annular wall, surrounding the aperture, and defining a shelf;
a clamp disposed on the shelf of the rim; and
a ventricular assist device, wherein the plate provides a mount for securing the ventricular assist device.

* * * * *